United States Patent [19]

Courtis

[11] 4,121,525
[45] Oct. 24, 1978

[54] METHOD AND APPARATUS FOR ASEPTICALLY SOWING SMALL SEED OR SPORES

[76] Inventor: William S. Courtis, 5801 Sunset La., Indianapolis, Ind. 46208

[21] Appl. No.: 783,679

[22] Filed: Apr. 1, 1977

[51] Int. Cl.² .............................................. A01G 1/00
[52] U.S. Cl. ....................................... 111/1; 195/120; 195/126; 215/248; 215/261; 47/1.1; 47/58; 47/59
[58] Field of Search ............... 195/120, 126, 127, 139, 195/142; 47/1.1, 1, 58; 111/1; 215/247-249, 261

[56] References Cited

U.S. PATENT DOCUMENTS

| | | | |
|---|---|---|---|
| 1,072,674 | 9/1913 | Tint | 215/248 |
| 2,153,981 | 4/1939 | Heineman | 215/248 |
| 2,186,908 | 1/1940 | Page et al. | 215/248 |
| 2,706,702 | 4/1955 | Carski | 195/126 |
| 2,851,821 | 9/1958 | Guiochon | 47/1.1 |

FOREIGN PATENT DOCUMENTS

| | | | |
|---|---|---|---|
| 47-20,390 | 6/1972 | Japan | 47/1.1 |
| 985,763 | 3/1965 | United Kingdom | 195/139 |
| 1,176,188 | 1/1970 | United Kingdom | 47/1.1 |

OTHER PUBLICATIONS

A simple method . . ., Harrison, Amer. Orchid Soc. Bull., Aug. 1970, pp. 715-716 relied on.

Primary Examiner—Robert E. Bagwill
Attorney, Agent, or Firm—Jenkins, Coffey & Hyland

[57] ABSTRACT

A method for aseptically sowing small seeds or spores of green plants includes preparation of a sterile closed flask (one-half pint jar) containing a growth medium and having both a contamination-resistant vent and a puncturable, resealing membrane in its closure. The seeds or spores are placed in a hypodermic syringe and a sterilizing solution is drawn into the syringe and held in contact with the seeds long enough to sterilize their surfaces. If desired, the sterilizing solution is ejected from the syringe through a filter or otherwise so as to retain the seeds or spores, and replaced by a wash liquid. The syringe is fitted with a sterile hypodermic needle of sufficient bore size to pass the seeds or spores. The needle is inserted through the membrane, after sterilizing the outside surface of the membrane, and the sterilized seeds or spores are discharged directly from the syringe onto the growth medium in the flask.

13 Claims, 4 Drawing Figures

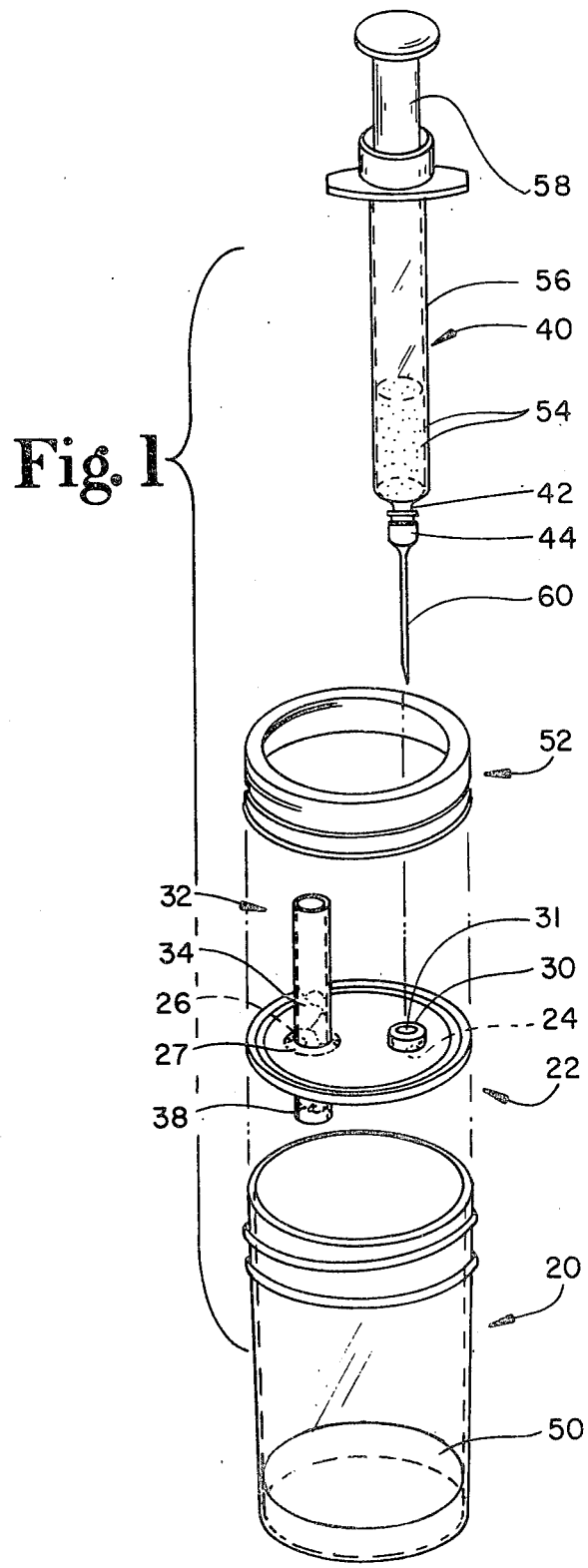
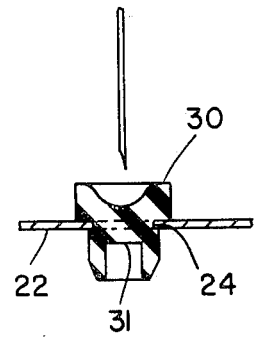
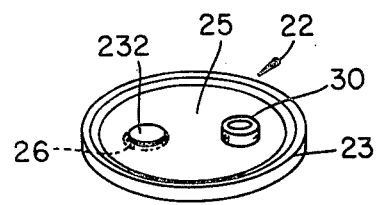
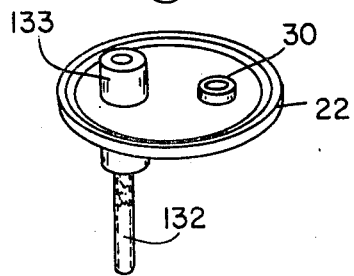

ID ANDAPPARATUS FOR ASEPTICALLY SOWING SMALL SEED OR SPORES

BACKGROUND OF THE INVENTION

This invention relates to a method and apparatus for aseptically sowing small seeds or spores, and particularly for sowing small seeds and small spores of green plants, for example, the seeds of orchids and cactus, and the spores of ferns. For convenience, the term "seeds" is hereinafter used to refer to both such seeds and spores. While the following description is directed generally to orchids, it is to be understood that this is by way of example and that the described method and apparatus will work equally as well with other small seeds or spores.

The growing of orchids from seeds, wherein an organic medium replaces a mycorhizal fungus, is a situation which requires an aseptic seed planting technique. Various time-consuming methods have been developed for aseptic planting of such seeds. These methods are commonly used by scientists and orchidologists. Illustrative methods are detailed in Lucke, "Sowing of Orchid Seed Made Easy", *American Orchid Society Bulletin* 44 (2): 109–118; and Simpson, "Raising Orchids from Seed", *The Orchid Review* 84 (984): 203–206. These methods are generally laborious and time-consuming. They require prepared culture flasks to be opened to sow the seed, and this raises the possibility of contamination by airborne spores, etc. Various tools have been developed to aid in such aseptic sowing. Such tools are described in, for example, Arditti, "A Flasking Tool for Orchid Seeds", *American Orchid Society Bulletin* 37: 425–426; Arditti, "Two Tools for Flasking Orchid Seeds", *The Orchid Review* 83 (890): 47–50; and Harrison, "A Simple Method for Flasking Orchid Seeds", *American Orchid Society Bulletin* 39: 715–716. While these are helpful, there is need to further reduce labor and time and the danger of contamination.

SUMMARY OF THE INVENTION

It is an object of the present invention to provide a method and apparatus for aseptically sowing small seeds and spores of green plants in a sterile closed flask prepared with a growth medium, which require less labor and time, and which avoids opening the flask to sow the seed. The possibility of contamination of the inside of the flask by airborne spores, bacteria, etc. is thereby greatly reduced.

In accordance with the invention, a wide-mouth flask, e.g., a canning jar, is prepared with a layer of growth medium. The flask is closed with a lid which has a first opening containing a venting element, such as a tube packed with cotton, and has a second opening closed with a stopper having a puncturable, self-resealing membrane. The flask containing the culture medium and the lid are sterilized in advance, and tightly closed. The seeds to be sown are sterilized by placing them in the barrel of hypodermic syringe and drawing sterilizing solution into the syringe and causing it to wet the surface of the seeds and remain in contact with the seeds for a time sufficient to sterilize their surfaces. The sterilized seeds are then sown on or in the growth medium by thrusting the needle of the syringe through the stopper membrane and discharging the seeds directly from the syringe into the flask. The seeds may then be discharged while still in the sterilizing solution, but if desired, the sterilizing solution may be removed and replaced with sterile wash liquid before the seeds are planted.

BRIEF DESCRIPTION OF THE DRAWINGS

The present invention may best be understood by referring to the following description and accompanying drawing, in which:

FIG. 1 is an exploded perspective view showing apparatus in accordance with the invention and useful for performing the method of the invention;

FIG. 2 is a cross section of a representative rubber stopper having a puncturable, resealing membrane;

FIG. 3 is a perspective view of a modified form of flask lid in which the vent tube is largely within the flask; and FIG. 4 is a perspective view of another modified flask lid in which the vent element is a small-pore filter pad.

DETAILED DESCRIPTION OF THE PREFERRED EMBODIMENT

The apparatus shown in FIG. 1 comprises a culture flask 20 in the form of a one-half pint, wide-mouth glass jar. Such jars are inexpensive and can be quickly and safely sterilized as required. Also, the wide-mouth is larger than the body of the jar, and this facilitates removal of the culture medium and the germinated seeds or spores.

The flask 20 is closed by a closure in the form of a lid 22 held in place by a threaded band 52. The lid 22 has two holes 24 and 26 formed therein. One hole 24 is closed by a stopper 30 having a membrane portion 31 adapted to be punctured by a hypodermic needle and to reseal itself when the needle is withdrawn. The other hole 26 is closed with a vent element, conveniently in the form of a vent tube 32 inserted into the hole 26 and sealed in place therein, as with silicone rubber cement 27. A thin layer of silicone rubber cement may also be applied over the lid sealing compound which extends about the downward periphery of lid 22, to extend the useful life of the lid. After the lid 22 is prepared and the cement has cured, a packing 34 of cotton is inserted in the vent tube 32. The cotton packing 34 does not extend to the inner end 38 of the vent tube, in order to prevent condensation of water on the cotton in the inner end of the vent tube 32 such as may lead to possible contamination.

A syringe 40 is used for planting seeds in the flask 20. Desirably, the syringe is a 10 ml. disposable plastic syringe having a locking tip 42 to which a needle 60 is removably locked. The tip should have a bore of adequate size to freely pass the seeds, and with commercial syringes it has been found desirable to drill out the tip to achieve the largest bore size consistent with maintaining the integrity of the locking function of the tip. Similarly, the needle 60 used is of large bore, and an eighteen gauge needle has been found satisfactory, particularly with orchid seeds. The syringe has a barrel 56 which slidably receives a plunger 58.

The method of aseptically planting seeds with the use of this apparatus is as follows: A desired amount of a culture medium 50 is placed in each unsterilized flask 20. Lids 22 are then placed on the flasks and are held in place by the screw-on bands 52. The flasks 20 are then sterilized, either singly or in batches, as in an autoclave or pressure cooker (not shown). Flasks for orchid seeds can be sterilized suitably by subjecting them to fifteen pounds per square inch gauge pressure for fifteen minutes in a pressure cooker. After the flasks 20 have been sterilized and allowed to cool, the screw-on bands 52 are tightened firmly to avoid contamination of the flasks before sowing and during culture.

Seeds or spores 54 to be sown are placed inside the barrel 56 of the hypodermic syringe 40 and the plunger 58 is inserted in the barrel. A quantity of sterilizing solution is drawn into the syringe for sterilizing the surfaces of the seeds or spores 54 contained therein. A suitable sterilizing solution for this purpose is a dilute chlorine bleach solution, for example, a calcium hypochlorite solution or the household bleach sold under the trademark "Chlorox". The tip 42 of the syringe is then closed and the surface sterilization of the seeds or spores 54 within the syringe is conducted. For orchids, a ten-minute sterilization in a 5-percent "Chlorox" bleach solution with agitation is sufficient. Since agitation is used, it is desirable to draw a small amount of air into the syringe after the sterilizing solution is drawn into it. Such mild sterilizing has not been found to impair germination of the seeds or spores 54 within the flask 20. While the seeds or spores are being sterilized, a quantity of sterilizing solution is also placed on the outside surface of the puncturable stopper 30 and allowed to remain so as to sterilize such surface.

After the sterilization step, a sterile hypodermic needle 60 is attached to the syringe, the air is expelled from the syringe, and sterilized seeds or spores 54 are then ready for sowing. The outside surface of the puncturable stopper 30 is wiped to remove excess sterilizing solution, and the needle 60 is then forced through the puncturable membrane 31. The seeds or spores are allowed to sink to the bottom of the syringe barrel 56 and into the bore of the needle 60. Slight, gentle depression of the plunger 58 will then cause a number of seeds or spores 54 to be dispensed onto the culture medium in the flask.

If approximately equal numbers of seeds are wanted in a series of flasks 20, the seeds can be suspended in the liquid and equal quantities of suspension injected successively in the flasks. To this end, air can be drawn into the syringe after the needle has penetrated the membrane 31 of a flask 20, and the syringe 40 and flask 20 can then be shaken to agitate the mixture and suspend the seeds fairly uniformly in the sterilizing solution. The same number of drops of this seed suspension can then be injected into the successive flasks 20.

If desired, the sterilizing solution may be removed from the seeds and replaced with another liquid, which may be referred to as a wash liquid. For this purpose, a fine sterile filter such as a "Swinney" filter unit with a "Millipore" or other fine-pore filter can be placed on the tip 42 of the syringe, and the sterilizing solution forced through the filter from the syringe. The small-pore filter will retain the seeds in the syringe. A wash solution, e.g., sterile distilled water, can then be drawn into the syringe. If a filter of sufficiently small pore size is used, e.g., 0.45 micron or smaller, the wash solution can be drawn into the syringe through the filter and need not be sterile. Alternatively, instead of using a smallpore filter, the syringe may be inverted and the seeds or spores allowed to sink to the plunger end of the syringe; and the sterilizing solution can then be expelled from the syringe and a sterile wash liquid drawn into the syringe. The seeds or spores are sown in such wash liquid as previously described.

If the seeds or spores being processed tend to float, they can be sown by inverting the flask 20 and syringe 40 after the needle has penetrated the membrane 31 of the closure member 30. Air is drawn into the syringe to clear the needle 60, and the seeds are allowed to float to the top of the liquid in the syringe. The seeds are then forced into the needle until the needle is filled. The flask and syringe are then turned upright and the seeds forced out of the needle onto the culture medium in the flask.

The advantages of this aseptic sowing method over previously described methods include the following: Any seed or spore that can withstand surface sterilization and is small enough to pass through a large-gauge hypodermic needle can be sown in this manner. Culture contamination is virtually impossible unless the flask 20, medium 50, or seed 54 is improperly sterilized. The seeds or spores can be sown quite rapidly. For example, twenty flasks can be sown from the same seed lot in less than 30 minutes. The entire method can be carried out in a normal room environment. This method thus obviates the need for a clean room or other expensive environmental control apparatus.

Other materials, such as growth regulators, metabolites, etc. can be added as desired to the sown flasks at any time by injecting sterile solutions of them with a hypodermic syringe and a small-gauge needle. A solution to be added to the culture flasks can be sterilized by passing it through a sufficiently fine-pore filter either as it is being drawn into the syringe or, preferably, as it is discharged from the syringe to a sterile needle inserted through the stopper into the culture flask. Samples of the cultured seeds or spores can be aseptically removed subsequent to sowing at any time until the growing plants become too large to be drawn into a hypodermic needle. If canning jars are used, as in the described embodiment, prepared lids will fit a variety of jar sizes and the jars can be reused indefinitely. The method and apparatus has been found especially advantageous in planting orchid seeds, but can be used with various other small seeds and spores, particularly spores of green plants.

The modified flask closure shown in FIG. 3 is a lid 22 like that of FIG. 1, and likewise containing two holes 24 and 26. The hole 24 is closed with a puncturable, resealing stopper 30 as in FIG. 1. The hole 26, however, contains a vent tube 132 which is differently mounted and arranged. The tube 132 is mounted by means of a sleeve 133 of soft rubber or the like which is compressed between the tube 132 and the edge of the hole 26 so as to support the tube in the hole and seal it to the web of the lid. In this case, and as shown, the tube is disposed largely below the lid so that the greater part of its length will be inside the flask and only a short top portion will stand above the lid. As will be understood, a tube so disposed can also be mounted with rubber cement as in FIG. 1, and the sleeve 133 may be used to mount a vent tube which is disposed as in FIG. 1.

The modified closure shown in FIG. 4 is similar to that of FIG. 1, in that it comprises a disk-shaped lid 22 having a peripheral portion 23 adapted to engage the lip of the wide-mouth jar 20 and provided with a lining of sealing compound to seal it to that lip. The central web 25 of the lid 22 contains two holes 24 and 26. The hole 24 is closed with a puncturable, resealing stopper 30 as before. The hole 26, however, is closed with a disk 232 of small-pore filter material, such as a pad of 0.45 micrometer pore size filter sheet available under the trademark "Millipore". The filter pad can be secured and sealed to the lid by cementing it in place with silicone rubber cement.

In use, the modified closures of FIGS. 3 and 4 replace the closure shown in FIG. 1, and the resulting apparatus is used in the same way as described in connection with FIG. 1.

What is claimed is:

1. The method of aseptically sowing small seeds and spores of green plants, comprising the steps of preparing a sterile flask with a growth medium therein and closed by a closure having a puncturable, resealing membrane, placing a quantity of the seeds or green-plant spores in a syringe barrel, treating the seeds or spores in the barrel with a surface sterilizing fluid adapted to destroy bacteria and fungal spores, injecting the so sterilized seeds or green-plant spores from the syringe barrel directly into the flask through a sterile needle attached to the syringe barrel and passed through the puncturable membrane.

2. The method of claim 1 wherein the step of surface sterilizing the seeds or green-plant spores in the syringe comprises the steps of placing the seeds or spores in the syringe barrel, drawing the sterilizing fluid into the syringe, and contacting the seeds or spores with such fluid in the syringe so as to sterilize the surfaces thereof.

3. The method of claim 2, further including the steps of ejecting the sterilizing fluid from the syringe while retaining the seeds or spores therein, and drawing a wash liquid into the syringe apparatus for admixture with the retained surface-sterilized seeds or spores.

4. The method of claim 3 wherein the seeds or spores are retained in the injection apparatus during ejection of the sterilizing fluid by means of a filter placed over the syringe outlet, the filter being of a pore size to pass the sterilizing fluid but not to pass the seeds or spores.

5. The method of claim 4 wherein the wash liquid is drawn through the filter into the injection apparatus.

6. The method of claim 5 wherein the filter pore size is sufficiently small to sterilize the wash liquid drawn therethrough.

7. The method of aseptically sowing small seeds and spores of green plants, comprising the steps of preparing a series of sterile closed flasks containing a growth medium and closed by closures each including a puncturable, resealing membrane, placing a quantity of the seeds or spores in the barrel of a syringe, surface sterilizing the same with a sterilizing fluid in the syringe barrel, and injecting quantities of the sterilized seeds or spores directly from the syringe barrel successively into the flasks through a sterile needle attached to the syringe and passed successively through the puncturable membranes of the series of flasks.

8. The method of claim 7 in which the seeds or green-plant spores are caused to be suspended in liquid in the syringe, and measured quantities of the liquid suspension are injected into the successive flasks from the syringe.

9. Apparatus for aseptically planting and culturing orchid seeds, comprising a flask containing a quantity of culture medium, a closure for closing the flask and having a gas impervious web across the mouth of the flask, said closure having a first opening closed by a venting element comprised of an elongated tube fixed in such opening and containing a cotton packing or the like intermediate its ends, and said closure having a second opening closed by means including a puncturable, resealing membrane adapted to be punctured by a hollow needle through which the orchid seeds can be discharged to the culture medium, and to reseal itself upon withdrawal of the needle so as to exclude contamination during subsequent culturing of the seeds, said flask with culturing medium therein, the closure, the venting element and closing means being adapted to be heat sterilized after assembly, and the sterilized assembly thereafter implanted with pre-sterilized seeds, so as to provide a sterile environment for subsequent germination and growth of the orchid seeds.

10. Apparatus as in claim 9 in which the tube projects upward from the closure so as to be largely disposed outside the flask.

11. Apparatus as in claim 9 in which the tube projects downward from the closure so as to be largely disposed inside the flask.

12. Apparatus as in claim 9 in which the flask is a wide-mouth jar and the closure is a removable lid in the form of a disk having an edge portion to sealingly engage the mouth of the jar and having a central web containing said first and second openings in spaced relation.

13. Apparatus as in claim 9 in which said means for closing said second opening comprises a puncturable stopper inserted in said second opening and sealingly engaged with the edge thereof.

* * * * *